(12) United States Patent
Karpitskiy et al.

(10) Patent No.: US 9,173,911 B2
(45) Date of Patent: Nov. 3, 2015

(54) METHOD FOR PRODUCING VEGETABLE CELL SAP CONCENTRATE AND MEANS FOR THE PRODUCTION THEREOF

(75) Inventors: Vladimir I. Karpitskiy, Tomsk (RU); Aleksandr K. Kurganov, Tomsk (RU)

(73) Assignees: OOO "SIBEX", Tomsk (RU); SOLAGRAN LIMITED, Melbourne (AU)

( * ) Notice: Subject to any disclaimer, the term of this patent is extended or adjusted under 35 U.S.C. 154(b) by 0 days.

(21) Appl. No.: 12/700,946

(22) Filed: Feb. 5, 2010

(65) Prior Publication Data

US 2010/0136149 A1 Jun. 3, 2010

Related U.S. Application Data

(63) Continuation of application No. PCT/RU2008/000483, filed on Jul. 22, 2008.

(30) Foreign Application Priority Data

Aug. 7, 2007 (RU) .................................. 2007130259

(51) Int. Cl.
*A61K 36/00* (2006.01)
*A23L 1/30* (2006.01)
*B01D 11/02* (2006.01)
*C11B 9/02* (2006.01)

(52) U.S. Cl.
CPC ................ *A61K 36/00* (2013.01); *A23L 1/3002* (2013.01); *B01D 11/0203* (2013.01); *C11B 9/025* (2013.01)

(58) Field of Classification Search
None
See application file for complete search history.

(56) References Cited

U.S. PATENT DOCUMENTS 4,104,409 A * 8/1978 Vitzthum et al. ............. 426/386
5,264,236 A * 11/1993 Ogasahara et al. ........... 426/600

FOREIGN PATENT DOCUMENTS

| RU | 2039586 C1 | 7/1995 |
|---|---|---|
| RU | 2061491 C1 | 6/1996 |
| RU | 2067977 C1 | 10/1996 |
| RU | 2125459 C1 | 1/1999 |
| RU | 16503 U1 | 1/2001 |
| RU | 2220614 C2 | 1/2004 |
| RU | 2238663 C2 | 10/2004 |
| RU | 2259991 C2 | 9/2005 |
| SU | 1346111 A1 | 10/1987 |
| WO | WO 2004110176 A1 * | 12/2004 |

OTHER PUBLICATIONS

Roshchin et al. "Carbon Dioxide Extract from Woody Verdure of the Scotch Pine Group Composition and Acids". Khima Prirodnykh Soedinenii, No. 4 (Jul.-Aug. 1988), pp. 447-452.*
Ushinova et al. "Isolation of Maltol from Siberian Fir Bark by the Carbon Dioxide Method". Chemistry of Natural Compounds, vol. 34, No. 1 (1998) pp. 131-132.*
Engineering Talk. Engineeringtalk editorial team. "Plunger pump is dedicated to liquid carbon dioxide". Apr. 18, 2005 [retrieved from the internet on: Dec. 16, 2010]. Retrieved from the Internet: < URL: http://www.engineeringtalk.com/news/caz/caz100.html>.*
Zeković et al. APTEFF (2003) 34, pp. 125-133.*
Ushanova et al. Chemistry of Natural Compounds, vol. 34, No. 1, 1998. 2 pages.*
Rozzi et al. Comprehensive Reviews in Food Science and Food Safety. vol. 1 (2002) 33-44.*
International Search Report, mailed Nov. 13, 2008, from International Application No. PCT/RU2008/000483 filed Jul. 22, 2007.

* cited by examiner

*Primary Examiner* — Amy L Clark
(74) *Attorney, Agent, or Firm* — Foley & Lardner LLP

(57) ABSTRACT

The invention relates to extracting biologically active substances from raw vegetable matter, consists in using a liquefied carbon dioxide and can be used in the pharmaceutical, perfume-and-cosmetic and food industries. The aim of the invention is to produce a cell sap concentrate by using liquefied carbon dioxide for the irradiation thereof. The inventive method consists in extracting a milled matter by means of liquefied carbonic acid at room temperature and in separating an oil fraction, wherein the extraction is carried out at a high rate of the liquefied carbonic acid with a proportion of not less than 11 of carbonic acid per 1 g of extracted vegetable cell sap and a vegetable cell sap concentrate is produced by separating the oil fraction from a water fraction.

2 Claims, No Drawings

METHOD FOR PRODUCING VEGETABLE CELL SAP CONCENTRATE AND MEANS FOR THE PRODUCTION THEREOF

RELATED APPLICATIONS

This application is a Continuation of International Application No. PCT/RU2008/000483 filed on Jul. 22, 2008, which claims priority to Russian Patent Application No. RU 2007130259 filed on Aug. 7, 2007, both of which are incorporated herein by reference in their entirety.

FIELD OF THE INVENTION

The invention relates to extracting biologically active substances from raw plant matter and is based on consists the use of liquefied carbon dioxide.

The invention can be used in the pharmaceutical, perfume-and-cosmetic, and food industries.

BACKGROUND OF THE INVENTION

The group of inventions applied for is intended for the production of an aqueous fraction of plants that represents an essentially natural concentrated cell sap extractable from the freshly collected plant by means of carbon dioxide. The concept "cell sap" is used in prior art.

It is known that cell sap is a liquid secreted by the cytoplasm of the living plant and filling its vacuoles. The cell sap, which consists of water with mineral and organic substances dissolved in it, is contained in the vacuoles. The cell sap is specific for the family and even the species of plants and depends on growing conditions, the age of the plant and of its individual cells. The accumulation of cell sap within the protoplasm is a purely physical process that can be reproduced artificially.

The production of aqueous fractions (extracts) of fir, sea-buckthorn, viburnum, etc. is known in prior art.

The methods of producing them are based, for example. on steam distillation of biologically active substances, extraction of plant raw materials by an organic solvent and dilution of the extract obtained by water, or by a water-ethanol mixture, and on carrying out extraction of plant raw materials under pressure in two stages.

Thus, in the known method of producing agents increasing the resistance of the body, the aqueous extract of fir is produced by treating the raw material by live steam for 1.5-2 hours, the vapor-gas mixture is carried off. and the aqueous extract separated from the oil.

A drawback of this method is the use of a high process temperature, which results in the destruction of vitamins and other biologically active compounds, as well as to the low stability of the extract produced.

The use of liquefied carbon dioxide as the extractant is known in prior art. Thus the extraction of plant raw materials by liquefied gases is accomplished under pressure in two stages, wherein the flow-through extraction is accomplished under pressure exceeding the filling pressure, and depressurization to the filling pressure is carried out between the stages. The conditions for implementing the method ensure effective drenching of the raw materials; this promotes an increase in the degree of extraction of the required components from the deep layers of the raw materials over a shorter time interval.

However, carotenoids, chlorophyll compounds, and other necessary components, for example, of the lipid fraction, are produced in this method as the desired biologically active components. At the same time, cell sap concentrate is not available as the desired product.

A method for producing extracts from plant raw materials using liquefied carbon dioxide is known. However, in this method the aqueous fraction of the plant raw materials is not segregated as a separate product and is not used to produce an aqueous fraction—cell sap concentrate.

The closest in technical essence and result to be achieved is a method for processing the.bark of coniferous trees, which includes milling, soaking, and extraction by liquefied carbon dioxide under increased pressure and at room temperature, with division into lipid and aqueous fractions, where the aqueous fraction is extracted by chloroform.

However, in this method the liquefied carbon dioxide is used not to produce cell sap in native form, but serves for the extraction of the water that is used at the beginning of the process for soaking the bark and for dissolving the maltol to be extracted from the bark of coniferous trees.

The analysis conducted has shown that the use of liquefied carbon dioxide to produce plant cell sap concentrate is not known in prior art.

SUMMARY OF THE INVENTION

The objective of the invention is to produce a cell sap concentrate by using liquefied carbon dioxide as the means for the production thereof.

The technical result is achievement of the possibility of producing a cell sap concentrate. Here, the yield and quality of the useful substances of plant raw materials are increased by producing a cell sap concentrate in native form.

The stated objective is achieved by the fact that in the known method, which includes extracting milled raw materials by means of liquefied carbon dioxide at room temperature and with separation of an oily fraction, wherein the extraction is carried out at a high flow rate of the liquefied carbon dioxide in a proportion of not less than 1 L of carbon dioxide per 1 g of extracted plant cell sap, and a plant cell sap concentrate is produced by separating the oily fraction from the aqueous fraction.

The technical result is achieved mainly as a result of the fact that liquefied carbon dioxide is used as the means for producing a plant cell sap concentrate.

The extraction of the raw materials is carried out preferentially by liquefied carbon dioxide in an extractor by means of the supply of liquefied carbon dioxide from a storage chamber mounted at a height no less than 8-12 m above the extractor.

The extraction of the raw materials by liquefied carbon dioxide may also be carried out by means of the supply of liquefied carbon dioxide by a dosing pump.

It is best to use freshly collected plant raw materials for the extraction.

Extraction by liquefied carbon dioxide ensures selective and sufficiently complete separation of cell sap in the form of an aqueous fraction from plant raw materials, since liquid carbon dioxide dissolves both water and water-soluble compounds. This is explained by the fact that the solubility of water in liquefied carbon dioxide is 0.1%, i.e., to produce 1 kg (or liter) of cell sap at the output it is necessary to pass 1,000 kg of liquefied carbon dioxide through the plant raw materials. Several tens of liters of liquefied carbon dioxide are sufficient to separate 1 kg of the oily fraction. Therefore, it is necessary for the separation of cell sap in the form of an aqueous fraction to pass a sufficiently large amount of liquefied carbon dioxide in the flow-through extractor. In the typical installations, the height of mounting of the liquefied carbon dioxide storage chamber is 0.5-1 m above the extractor; therefore the flow of extractant is sufficient for the separation of the oily fraction, but insufficient for the separation of the aqueous fraction. According to the proposed invention, the flow of carbon dioxide can be achieved as a result of the height of the liquid column. This is achieved structurally by the creation of a pressure gradient through elevation of the liquefied carbon dioxide storage chamber 8-12 m above the extractor. This objective can also be achieved by the use of a high-pressure pump. The extraction process takes place at room temperature; this does not result in destructive alterations of the chemical compounds, and the cell sap extracted from freshly collected plant raw materials by means of liquefied carbon dioxide under pressure without temperature conditioning is represented in native form.

At the same time, in the group of inventions applied for, water is not added at any stage of the extraction process to produce the aqueous fraction of the plant raw materials. Consequently, the aqueous extract consists of natural cell sap of the plant subjected to extraction that contains a whole complex of biologically active substances.

The use of liquefied carbon dioxide to carry out an extraction process is known; however, its use to produce cell sap concentrate was not found in prior art. Extraction of volatile oils and other fat-soluble plant components from plant raw materials with the aid of liquefied carbon dioxide is generally recognized. However, water and water-soluble substances of plants dissolve in liquefied carbon dioxide to a small extent, water (0.1%). When the extraction process is completed and carbon dioxide gas is removed by depressurization, the water and water-soluble substances are repelled by the oily fraction and are segregated into a separate phase. Since the quantity of water and water-soluble substances in the known technical solutions is vanishingly small, and, as a rule, the oily fraction is the desired product, information on aqueous fractions extracted by means of liquefied carbon dioxide was not found in the scientific and technical patent literature. Consequently, the group of inventions applied for satisfies the "novelty" and "inventive level" criteria.

The above and other features of the invention including various novel details of construction and combinations of parts, and other advantages, will now be more particularly described and pointed out in the claims. It will be understood that the particular method and device embodying the invention are shown by way of illustration and not as a limitation of the invention. The principles and features of this invention may be employed in various and numerous embodiments without departing from the scope of the invention.

DETAILED DESCRIPTION OF THE PREFERRED EMBODIMENTS

A method for the extraction of an aqueous extract of fir is implemented in the following manner.

Milled vegetation stock, preferably freshly collected, is exhaustively extracted by liquefied carbon dioxide at room temperature and at a pressure of 64±6 atm (3 hours is sufficient extraction time) in a flow-through extractor with increased flow of the liquid carbon dioxide through elevation of the liquefied carbon dioxide storage chamber 8-12 meters above the extractor. The increase in the flow of the liquid carbon dioxide through the plant raw materials to be extracted is achieved by increasing the column of the liquid carbon dioxide above the extractor, as a result of which the pressure of the liquid column on the raw materials is proportionally increased. Experimental studies have shown that when the liquid column is increased from 0.5-1 meter, which is typically used in standard installations and in the prototype (for the extraction of other desired products, for example, of an oily fraction) to 8-12 meters, flow increases accordingly 8-24-fold, and the pressure increases, which results in a proportional increase in the quantity of water and water-soluble substances extracted.

The increase in the flow of the liquid carbon dioxide through the plant raw materials to be extracted may also be achieved with the use of a dosing pump. After the carbon dioxide extract is obtained, the carbon dioxide gas is removed and a crude extract is obtained, which is divided into two fractions, oily and aqueous, by settling or centrifugation. The yield of the aqueous fraction of the carbon dioxide extract of the vegetation comprises cell sap with a high concentration of biologically active substances. The use of the proposed method makes it possible to produce an extract of water-soluble compounds of plants, cell sap without diminution of their biological activity. This is explained by the fact that carbon dioxide extraction of plant raw materials does not result in any destructive alterations of organic molecules, because the process takes place at room temperature, and that carbon dioxide gas is generally considered an inert gas.

The concentration of cell sap by means of the carbon dioxide employed is explained by the following. Let us consider the process of the concentration of intracellular sap in carbon dioxide extraction as exemplified by the Siberian fir, as the most frequently used raw material for the production of a carbon dioxide extract of fir. These considerations are applicable to any other plant. About 600 kg of water (the moisture content of freshly collected Siberian fir is 55-65%) are contained in 1000 kg of freshly collected Siberian fir. Experimental data have shown that approximately 0.6 kg of water-soluble biologically active components, namely ascorbic acid, maltol, organic salts, etc., are contained in said raw material. If it is assumed hypothetically that complete extraction of these compounds along with the water has taken place, then intracellular plant sap is obtained (600 kg with 0.1% dry residue). Experiments done with the method and means applied for have shown that 1 kg of water and 0.6 kg of water-soluble compounds are extracted after the passage of 1000 kg of liquid carbon dioxide, i.e., the method makes it possible to produce intracellular plant sap concentrate containing practically all the water-soluble components of the plant. Analysis carried out has shown the virtual absence of ascorbic acid and maltol in the raw material that has undergone extraction; this attests to the complete extraction of water-soluble components; this corresponds to the cell sap content. Experimental studies also showed that the plant sap concentrate produced has a dry residue numerical value of 3%; this attests to a 30-fold increase in the concentration of dissolved substances in the cell sap concentrate. If further extraction is continued, essentially only water is additionally extracted (1 kg for each 1000 kg of carbon dioxide). For complete extraction of water from 1000 kg of Siberian fir, 600,000 kg of liquid carbon dioxide would have to be passed through the raw materials to be extracted, which is practically unrealistic and unnecessary.

The process of carbon dioxide extraction does not depend or is weakly correlated with temperature and pressure. The pressure above the liquid carbon dioxide depends uniquely on the temperature, i.e., as temperature increases, pressure increases proportionally as well. Room temperature, which is as a rule within the limits of 15-30° C., corresponds to a pressure of 40-74 atm.

The practical realization of the method is illustrated by the following examples.

Example 1 (Analog)

Freshly collected and milled woody verdure of Siberian fir (58 kg) is subjected to steam distillation at a temperature of 100-180° C. and pressure of 1-2 atm for 10-24 hours. The yield of volatile oil is 1.45 kg (2.5% of the weight of the initial woody verdure). The yield of the aqueous fraction is 45 kg. The aqueous fraction contains 0.009% dry residue.

Example 2

Woody verdure of Siberian fir (58 kg), dried and milled to particles no greater than 5 mm in size, are extracted in a flow-through extractor with a column height of 0.5 m by liquefied carbon dioxide at a temperature of 20° C. and a pressure of 64 atm for 3 hours. The yield is 1.8 kg (3.1% of the weight of the initial woody verdure). An aqueous fraction is absent.

Example 3 (Prototype)

Freshly collected and milled woody verdure of Siberian fir (58 kg) is extracted in a standard flow-through extractor by liquefied carbon dioxide at a temperature of 20° C. and a pressure of 64 atm for 3 hours. The yield is 1.2 kg (2.1% of the weight of the initial woody verdure) of oily fraction. The aqueous fraction in a quantity of 80 g produces an emulsion with the oily fraction, is considered waste, and after settling or centrifugation is usually discarded in the form of a moist solid product used for extraction of maltol. The quantity of water is determined by the gravimetric method when the moist solid "maltol pulp" is dried out. By calculation the total flow-through of liquefied carbon dioxide is 80 liters.

Example 4

Freshly collected and milled woody verdure of Siberian fir (58 kg) is extracted in a flow-through extractor by liquefied carbon dioxide with a large flow-through of liquefied carbon dioxide by elevation of the liquefied carbon dioxide storage chamber to a height of 10 m above the extractor at a temperature of 20° C. and a pressure of 64 atm for 3 hours. The yield of crude extract is 2.3 kg (4.0% of the weight of the initial woody verdure). Two fractions are obtained after settling or centrifugation—an oily fraction of 1.4 kg (4%) and an aqueous fraction of 0.9 kg (1.6%). By calculation the total flow-through of liquefied carbon dioxide was 900 liters.

The product produced according to example 4 has the appearance of a dark red solution, soluble in water and alcohol. The dry residue is 2.9%, i.e., by content of dissolved substances, this product exceeds the known methods, in which the dry residue does not exceed 0.016 (according to the source), approximately 300-fold. Ascorbic acid content is 750 mg/kg.

Example 5

Freshly collected and milled woody verdure of Siberian fir (58 kg) is extracted in a flow-through extractor by liquefied carbon dioxide with a large flow-through of liquefied carbon dioxide by elevation of the liquefied carbon dioxide storage chamber to a height of 8 m above the extractor at a temperature of 20° C. and a pressure of 64 atm for 3 hours. The yield of crude extract is 2.1 kg (3.6% of the weight of the initial woody verdure). Two fractions are obtained after settling or centrifugation—an oily fraction of 1.4 kg (2.4%) and an aqueous fraction of 0.7 kg (1.6%). By calculation the total flow-through of liquefied carbon dioxide was 700 liters.

Example 6

Freshly collected and milled woody verdure of Siberian fir (58 kg) is extracted in a flow-through extractor by liquefied carbon dioxide with a large flow-through of liquefied carbon dioxide by elevation of the liquefied carbon dioxide storage chamber to a height of 12 m above the extractor at a temperature of 20° C. and a pressure of 64 atm for 3 hours. The yield of crude extract is 2.5 kg (4.3% of the weight of the initial woody verdure). Two fractions are obtained after settling or centrifugation—an oily fraction of 1.4 kg (2.4%) and an aqueous fraction of 1.1 kg (1.9%). By calculation the total flow-through of liquefied carbon dioxide was 1100 liters.

Example 7

Freshly collected birch leaf verdure in a quantity of 2.7 kg is processed as in example 4. The yield of crude extract is 52 g. Two fractions are obtained after centrifugation—an oily fraction of 21 g and an aqueous fraction of 31 g.

Example 8

Freshly collected nettle verdure in a quantity of 9.2 kg is processed as in example 4. The yield of crude extract is 802 g. Two fractions are obtained after centrifugation—an oily fraction of 482 g and an aqueous fraction of 320 g.

Example 9

Freshly collected cow-berry leaf verdure in a quantity of 6.7 kg is processed as in example 4. The yield of crude extract is 680 g. Two fractions are obtained after centrifugation—an oily fraction of 8 g and an aqueous fraction of 672 g.

Example 10

Freshly collected currant leaf verdure in a quantity of 8.2 kg is processed as in example 4. The yield of crude extract is 97 g. Two fractions are obtained after centrifugation—an oily fraction of 74 g and an aqueous fraction of 23 g.

Example 11

Sea-buckthorn berry pulp in a quantity of 9.7 kg is processed as in example 4. The yield of crude extract is 286 g. Two fractions are obtained after centrifugation—an oily fraction of 3 g and an aqueous fraction of 283 g.

Example 12

Viburnum berry pulp in a quantity of 6.87 kg is processed as in example 4. The yield of crude extract is 135 g. Two fractions are obtained after centrifugation—an oily fraction of 92 g and an aqueous fraction of 42 g.

Example 13

Freshly collected and milled woody verdure of Siberian fir (58 kg) are extracted in a flow-through extractor by liquefied carbon dioxide with a large flow-through of liquefied carbon dioxide using a high-pressure fluid pump at a set delivery rate of 100 L/hour, at a temperature of 20° C. and a pressure of 64 atm for 3 hours. The yield of crude extract is 1.7 kg (2.9% of the weight of the initial woody verdure). Two fractions are obtained after settling or centrifugation—an oily fraction of 1.4 kg (4%) and an aqueous fraction of 0.3 kg (0.5%). By calculation the total flow-through of liquefied carbon dioxide was 300 liters.

The product produced according to example 13 has the appearance of a dark red solution, soluble in water and alcohol. The dry residue is 3.0%.

Example 14

Woody verdure of Siberian fir (58 kg), freshly collected and milled to particles no greater than 5 mm in size, is extracted in a flow-through extractor by liquefied carbon dioxide with a large flow-through of liquefied carbon dioxide using a high-pressure fluid pump at a set delivery rate of 300 L/hour, at a temperature of 20° C. and a pressure of 64 atm for 3 hours. The yield of crude extract is 2.3 kg (4.0% of the weight of the initial woody verdure). Two fractions are obtained after settling or centrifugation—an oily fraction of 1.4 kg (4%) and an aqueous fraction of 0.9 kg (1.6%). By calculation the total flow-through of liquefied carbon dioxide was 900 liters.

The product produced according to example 14 has the appearance of a dark red solution, soluble in water and alcohol. The dry residue is 2.9%.

The experiments that were conducted and subsequent experimental-industrial implementation of the method for producing cell sap concentrate based on the use of a large volume of liquefied carbon dioxide demonstrated the high efficiency of the method. With regard to the dry residue, in which all active substances are concentrated, the aqueous fraction of the carbon dioxide extract of the plant raw materials that comprises the cell sap concentrate surpasses all known analogs obtained by other methods for producing aqueous fractions.

Industrial Applicability

The use of liquefied carbon dioxide according to the claimed method made it possible to produce an aqueous fraction of plants that is the intracellular water of the plant itself with the biologically active substances dissolved in it in concentrated form, i.e., cell sap concentrate. Given this, the cell sap contains useful natural substances in native (live) form in the maximal, concentrated amount. The invention applied for can be used in the pharmaceutical, perfume-and-cosmetic, and food industry.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing plant cell sap concentrate from Siberian fir comprising the steps of:
    milling freshly collected woody verdure of Siberian fir;
    extracting the milled woody vendure in a flow-through extractor at a temperature of 20° C. and a pressure of 64 atmospheres for 3 hours using liquefied carbon dioxide, wherein the liquefied carbon dioxide is added from a storage chamber that is elevated at a height of at least 8 meters above the extractor, to provide an oily fraction and an aqueous fraction, wherein the aqueous fraction is the plant cell sap concentrate;
    separating the oily fraction from the plant cell sap concentrate; and
    collecting the plant cell sap concentrate;
    wherein no water is added to the woody verdure of Siberian fir before or during the extracting step.

2. The method of claim 1, wherein the extracting step is carried out in the extractor by adding the liquefied carbon dioxide into the extractor by a dosing pump.

* * * * *